United States Patent [19]

Bishop

[11] Patent Number: 4,618,994
[45] Date of Patent: Oct. 21, 1986

[54] TAPS

[75] Inventor: David C. Bishop, Portslade, England

[73] Assignee: Smiths Industries Public Limited Company, London, England

[21] Appl. No.: 636,826

[22] Filed: Aug. 1, 1984

[30] Foreign Application Priority Data

Aug. 2, 1983 [GB] United Kingdom ............... 8320783

[51] Int. Cl.⁴ .................. B65D 33/16; B65D 33/38
[52] U.S. Cl. ........................ 383/96; 383/66; 383/904; 383/906
[58] Field of Search ............ 383/80, 66, 96, 904, 383/906; 604/335

[56] References Cited

U.S. PATENT DOCUMENTS

| 2,499,150 | 2/1950 | Lobl | 383/66 |
| 2,777,490 | 1/1957 | Munk | 383/66 |
| 2,891,704 | 6/1959 | Morrison | 383/80 |
| 4,055,179 | 10/1977 | Manschot et al. | 604/335 |
| 4,300,560 | 11/1981 | Steer et al. | 604/335 |

Primary Examiner—Stephen P. Garbe
Attorney, Agent, or Firm—McAulay, Fields, Fisher, Goldstein & Nissen

[57] ABSTRACT

A tap for a urostomy or similar bag has a first valve member which includes a male valve element located in a cap. The cap has at least one drainage hole. A second valve member including a tubular female valve element is engageable with the male valve element to close the tap, but is disengageable from the male valve element to open the tap. Flexible and/or extendible diaphragm or sheath is secured to and encloses part of the female valve element in a fluid-tight manner and is also connected to the cap in a fluid-tight manner. The diaphragm or sheath permits relative movement between the two valve members.

5 Claims, 3 Drawing Figures

TAPS

BACKGROUND TO THE INVENTION

A urostomy bag is a urinary drainage or diversion bag. Such bags are commonly made from flexible plastics material to receive urine or other fluid from the body of a patient. It is an object of the present invention to provide a tap for such a bag which can be opened or closed easily, is relatively inexpensive to produce and is efficient in use.

BRIEF SUMMARY OF THE INVENTION

The present invention provides a tap comprising a first valve member including a male valve element located in a cap having a drainage hole leading into the cap, a second valve member including a tubular female valve element which is engageable with the male valve element to close the tap, but which is disengageable from the male valve element to open the tap and a flexible sheath which is secured to and encloses part of the female valve element and which is connected to the cap in a fluid-tight manner and permits relative movement between the two valve members. The invention also provides a urostomy bag or other container for liquids incorporating such a tap.

BRIEF DESCRIPTION OF THE ACCOMPANYING DRAWINGS

FIG. 1 is a sectional view of a tap according to the invention fixed to a urostomy bag, FIG. 2 is a similar view of a modified construction, and FIG. 3 illustrates a urostomy bag having a tap according to the invention.

DESCRIPTION OF PREFERRED EMBODIMENTS

Figure 1:
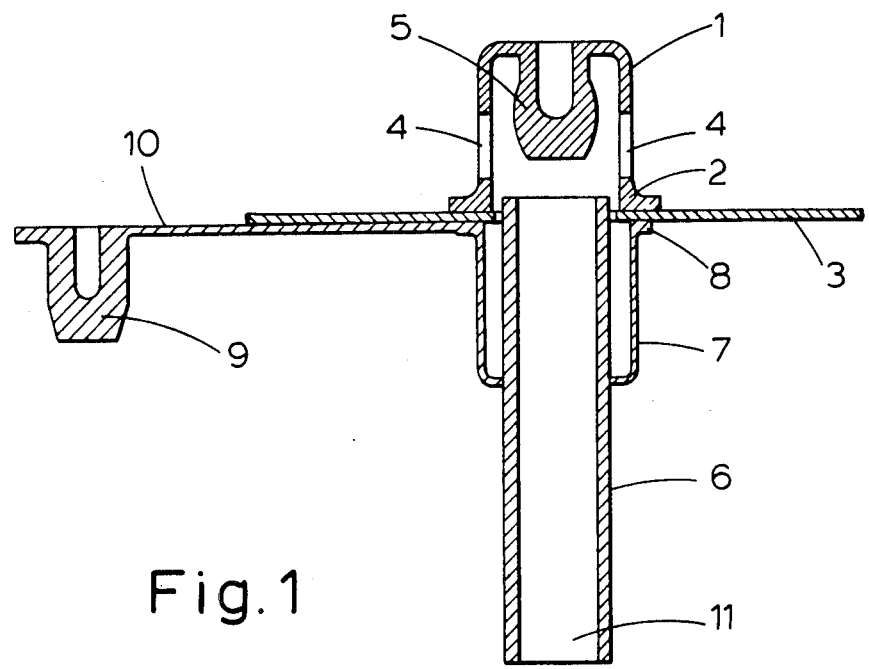

The tap illustrated comprises a first valve member including a cap or sleeve 1 which is open at one end and has an outwardly directed rim or flange 2 which enables the valve member to be secured to the flexible plastics material 3 of the bag. The cap or sleeve 1 has at least one drain hole, there preferably being two such holes 4 located opposite one another. A male valve element or plug 5 forms part of the cap or sleeve 1.

A second valve member comprises a female valve element 6 which also forms an outlet tube of the tap. A flexible, collapsible and/or extendible sheath or diaphragm 7 encloses a portion of the tubular valve element 6 and is secured to it in a fluid-tight manner. The sheath 7 has a rigid or semi-rigid ring 8 by which it can be sealed in a fluid-tight manner directly to the rim or flange 2 of the first valve member and the material 3 of the bag as illustrated in the drawing. The fluid-tight connections are conveniently achieved by radio-frequency welding, or by heat sealing or by any other suitable means.

When the valve members and the sheath are assembled, the sheath 7 cooperates with the cap or sleeve 1. In the embodiment illustrated in FIG. 1, the flexible material 3 of the bag is located between the flange 2 and the ring 8. In the embodiment illustrated in FIG. 2, (which is the preferred embodiment) the material 3 is secured to the upper surface of the flange 2.

Figure 2:
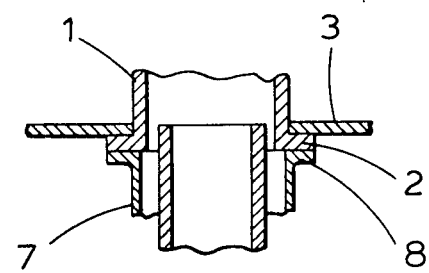

When the valve is in the opened condition as illustrated in FIG. 1, the female valve element 6 is disengaged from the male element 5. The female element can be disengaged from the male element simply by pulling the female element. In this open condition, the liquid contents of the bag 3 can drain through the drain holes 4 and flow out through the open ends of the female element or outlet tube 6.

When the tap is to be closed the female valve element 6 is simply pushed onto the male member 5 so that the passage of liquid through the tube 6 is prevented.

If desired, a second male closure plug 9 may be provided to fit into the outlet end 11 of the female valve element 6 thereby to provide a second closure. This plug is connected with the ring 8 by an integral strap 10. The plug provides additional security of closure for the patient when the tap is in its closed position.

The component parts of the tap are made from plastics material such as polyvinyl chloride, the cap or sleeve and male valve element preferably being of a more rigid material than the other components.

Figure 3:
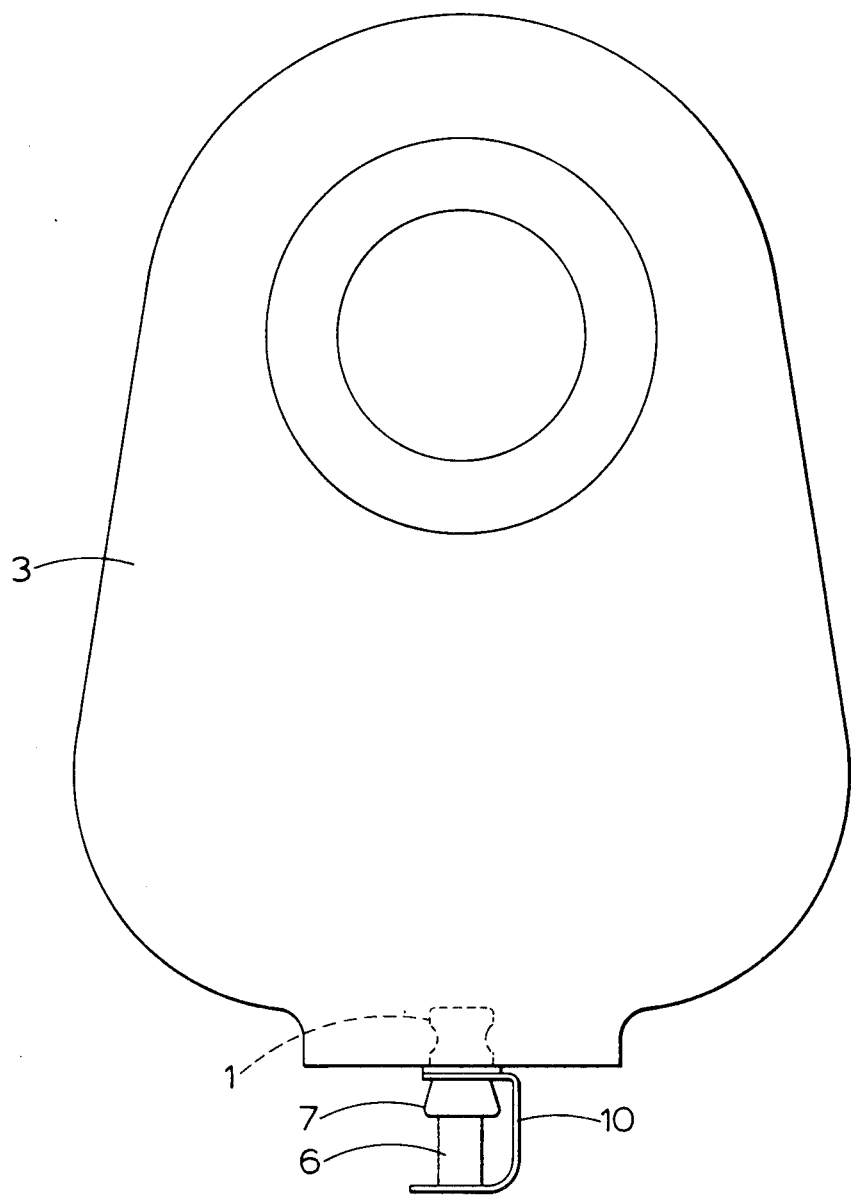

FIG. 3 illustrates the application of the tap to a urostomy bag, the plug 9 being in its closed position.

I claim:

1. A container for liquids having a tap comprising a first valve member including a cap secured to the container and having a drainage hole leading into the cap and a male valve plug in the cap; a second valve member including a tubular female valve element which is engageable with the male valve plug to close the tap, but which is disengageable to open the tap, and a flexible sheath which is secured to and encloses part of the female valve element and which is connected with the cap in a fluid-tight manner and permits relative movement between the two valve members.

2. A container as claimed in claim 1 made of flexible plastics material.

3. A tap comprising a first valve member including a male valve element located in a cap having at least one drainage hole leading into the cap, a second valve member including a tubular female valve element which is engageable with the male valve element to close the tap, but which is disengageable from the male valve element to open the tap, and a flexible sheath which is secured to and encloses part of the female valve element and which is connected to the cap in a fluid-tight manner and permits relative movement between the two valve members.

4. A tap as claimed in claim 3 wherein the cap has an open end provided with an outwardly directed flange by which the cap may be secured to a urostomy bag or the like and also has a plurality of drainage holes, a male valve plug forms part of the cap, the female valve element is an outlet tube in which the male valve plug may be engaged to prevent passage of liquid through the outlet tube, and the sheath is of flexible plastics material provided with a ring connected to the flange of the cap in a fluid-tight manner.

5. A tap as claimed in claim 3 wherein said outlet tube has an outlet end, and a second male closure plug is connected to the ring of the sheath via a strap and is engageable in the outlet end of the female valve element.

* * * * *